United States Patent
Khandelwal et al.

(10) Patent No.: US 7,803,402 B2
(45) Date of Patent: Sep. 28, 2010

(54) PHARMACEUTICAL PREPARATIONS

(76) Inventors: Sanjeev Khandelwal, Prem Nivas, 13, Altamount Road, Mumbai 400026 (IN); Pratibha Omray, 501, Redwoods, Vasant Garden Mulund (West), Mumbai 400080 (IN)

( * ) Notice: Subject to any disclaimer, the term of this patent is extended or adjusted under 35 U.S.C. 154(b) by 136 days.

(21) Appl. No.: 10/456,690

(22) Filed: Jun. 6, 2003

(65) Prior Publication Data

US 2004/0005361 A1    Jan. 8, 2004

(30) Foreign Application Priority Data

Jul. 6, 2002    (IN) .................. 506/MUM/2002

(51) Int. Cl.
 *A61K 9/20* (2006.01)
 *A61K 9/28* (2006.01)
 *A61K 9/38* (2006.01)
 *A61K 9/42* (2006.01)

(52) U.S. Cl. .............. 424/464; 424/474; 424/476; 424/477; 424/479; 424/480

(58) Field of Classification Search .......... 424/464, 424/465, 468, 469, 472, 479, 480, 488, 494, 424/476, 477
See application file for complete search history.

(56) References Cited

U.S. PATENT DOCUMENTS

| 4,756,911 | A | * | 7/1988 | Drost et al. ............... 424/468 |
| 5,514,383 | A | * | 5/1996 | Laly et al. ................ 424/464 |
| 5,783,215 | A | * | 7/1998 | Arwidsson et al. ......... 424/501 |
| 6,350,471 | B1 | * | 2/2002 | Seth ....................... 424/480 |
| 6,399,086 | B1 | * | 6/2002 | Katzhendler et al. ....... 424/405 |
| 6,669,948 | B2 | * | 12/2003 | Rudnic et al. ............. 424/400 |
| 6,908,626 | B2 | * | 6/2005 | Cooper et al. ............. 424/489 |
| 2003/0045522 | A1 | * | 3/2003 | Geczy .................... 514/236.2 |

FOREIGN PATENT DOCUMENTS

WO    WO 0162256    *    8/2001

OTHER PUBLICATIONS

Chemical Abstract, vol. 109, No. 12, Abstract No. 98626a, Jun. 1988.*

* cited by examiner

*Primary Examiner*—Mina Haghighatian
(74) *Attorney, Agent, or Firm*—Lucas & Mercanti, LLP

(57) ABSTRACT

A pharmaceutical extended-release oral drug delivery system comprising as active ingredient Cefixime Trihydrate in combination with a hydrophilic matrix system, and optionally containing additional pharmaceutically acceptable constituents, wherein at least 20% up to but not more than 40% of Cefixime Trihydrate is released from said matrix within 1 hour from oral administration and the remainder of the pharmaceutical agent is released at a sustained rate.

9 Claims, 4 Drawing Sheets

PHARMACEUTICAL PREPARATIONS

BACKGROUND OF THE INVENTION

The invention relates to pharmaceutical compositions in the form of tablets which contain cefixime and for a process of making the same.

In particular, this invention relates to a drug delivery system for delivering cefixime.

Cefixime is hygroscopic, slightly soluble in water; sparingly soluble in dehydrated alcohol; practically insoluble in ethyl acetate; freely soluble in methyl alcohol. A 5% suspension in water has a pH of 2.6 to 4.1.

Cefixime is a cephalosporin antibiotic, which can be administered orally and resembles, in respect of its structure, the spectrum of organisms and the beta-lactamase stability, the 3rd generation cephalosporins of the cefotaxime type, which can be administered parent rally. The introduction of an acid substituent into the 7.beta.-side chain of aminothiazolyl-cephalosporins, as, for example, in cefixime, leads to a compound, which can be absorbed enterally.

Like all representatives of this class of substances, it has a bactericidal action. The mechanism of action of cefixime is based on inhibition of bacterial cell wall synthesis. The acute toxicity of cefixime is negligibly low. Cefixime is stable to hydrolysis by many beta-lactamases. It has a mode of action and spectrum of activity similar to that of the third-generation cephalosporin cefotaxime but some Enterobacteriaceae are less susceptible to cefixime. *Haemophilus influenzae, Moraxella* (Branhamella) *catarrhalis*, and *Neisseria gonorrhoeae* are sensitive, including penicillinase-producing strains. Of the Gram-positive bacteria, streptococci are sensitive to cefixime but most strains of *staphylococci, enterococci*, and *Listeria* spp. are not.

Only 40 to 50% of an oral dose of cefixime is absorbed from the gastrointestinal tract, whether taken before or after meals, although the rate of absorption may be decreased in the presence of food. Conventionally, cefixime is better absorbed from oral suspension than from tablets. Absorption is fairly slow. Peak plasma concentrations of 2 to 3 micrograms per mL and 3.7 to 4.6 micrograms per mL have been reported between 2 and 6 hours after single doses of 200 and 400 mg, respectively. The plasma half-life is usually about 3 to 4 hours and may be prolonged when there is renal impairment. About 65% of cefixime in the circulation is bound to plasma proteins. Information on the distribution of cefixime in body tissues and fluids is limited. It crosses the placenta. Relatively high concentrations may be achieved in bile and urine. About 20% of an oral dose (or 50% of an absorbed dose) is excreted unchanged in the urine within 24 hours. Up to 60% may be eliminated by nonrenal mechanisms; there is no evidence of metabolism but some is probably excreted into the faeces from bile. It is not substantially removed by dialysis.

Cefixime is suitable for the treatment of acute and chronic infections of varying severity caused by cefixime-sensitive pathogens and amenable to oral therapy.

Cefixime has bactericidal effects and is effective, for example, for the following pathogens: *Streptococcus pneumoniae, Streptococcus pyogenes, Streptococcus agalactiae; Hamophilus influenzae, Neisseria gonorrhoeae, Escherichia coli, Proteus mirabilis, Proteus vulgaris, Klebsiella pneumoniae, Klebsiella oxytoca, Enterobacter* sp., *Pasteurella multocida, Providencia* sp., *Salmonella* sp., *Shigella* sp., *Citrobacter amalonaticus, Citrobacter diversus, Serratia marcescens.*

Cefixime-containing compositions are used only in the form of solid dosage forms such as tablets, capsules, granules or powders.

DETAILED DESCRIPTION OF THE INVENTION

Figure 1:
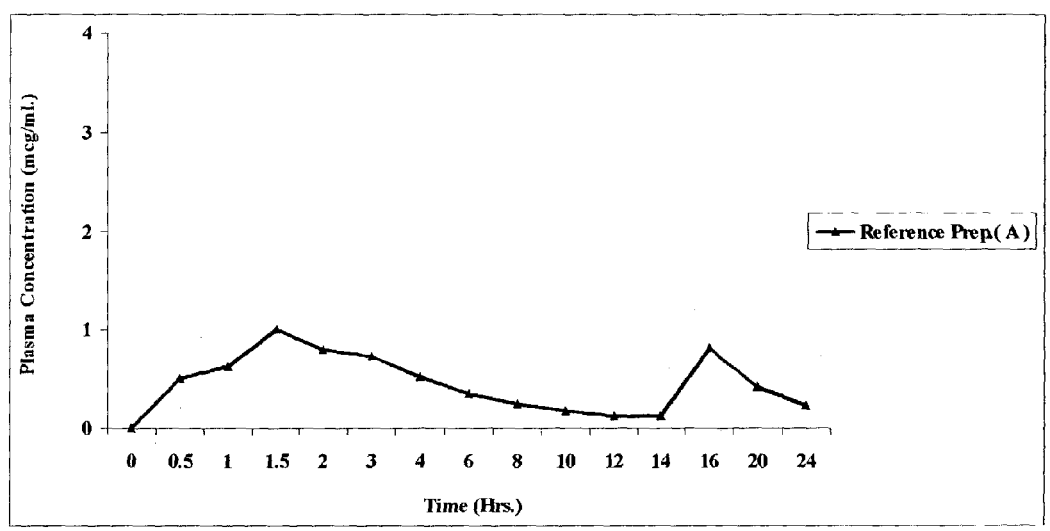
FIG. 1 illustrates plasma concentrations resulting from administration of a cefixime tablet administered twice-daily.

Particularly, this invention relates to extended-release oral drug delivery system comprising as active ingredient Cefixime Trihydrate.

This invention relates to a novel delivery system for cefixime. Cefixime is generally available in 200 mg strength and 2 to 3 tablets are recommended. The prior dosage has been done keeping in mind that the daily dose is maintained to a maximum of 400 mg only.

An efficient delivery system for a drug depends upon its pharmacokinetic properties such as absorption characteristics, protein binding and clearance, and pharmacodynamic parameters such as the concentration-effect relationship.

When dealing with anti-microbial agents such as cefixime the selection of a drug delivery system depends mainly on the immune system of the host. Unlike aminoglycosides, in the case of beta lactam antibiotics its antimicrobial activity is not dependent on its concentration. Again, unlike aminoglycosides, the kinetics of the bacteriocidal effect is slow and requires maintenance of drug effective concentration for a certain lag time to the onset of effect.

The biological half-life of cefixime is considerably short and therefore in the prior art 2 daily administrations are recommended. A minimum plasma concentration is necessary for a bacteriocidal activity. However, it is established that increasing the drug concentration above this base value does not correspondingly increase bacteriocidal activity although continuous infusion is preferable to periodic administration. In fact, high concentrations are counter productive and associated with reduced potency. There is no correlation between drug penetration and serum concentration.

Therefore, an oral sustained-release preparation that can maintain low but effective concentrations for a prolonged period will be a suitable mode of administration.

According to this invention there is provided a pharmaceutical extended-release oral drug delivery system for the active ingredient Cefixime Trihydrate comprising combining cefixime trihydrate with a hydrophilic matrix system, and optionally adding therein additional pharmaceutically acceptable constituents, wherein at least 20% up to but not more than 40% of Cefixime Trihydrate is released from said matrix within 1 hour from oral administration and the remainder of the active ingredient is released at a sustained rate.

The novel feature of the invention is to provide a once a day dosage of cefixime fixed at Cefixime U.S.P. 400 mg and there is no fear of exceeding the recommended daily dose.

The hydrophilic polymer selected from the group consisting of hydrophilic cellulose derivatives.

Typically, the hydrophilic polymer selected from the group consisting of hydrophilic cellulose derivatives methyl cellulose, hydroxypropyl methylcellulose, hydroxyethyl cellulose, hydroxypropyl cellulose, carboxymethyl cellulose, sodium carboxymethyl cellulose and hydroxyethyl methyl cellulose, hydrophilic polyacrylamide derivatives, proteins, alginates, arabinogalactane, chitosan and hydrophilic methacrylic acid derivatives.

The drug delivery system of the invention may further comprise a flavonoid to improve the absorption of the drug.

The hydrophilic matrix may comprise a hydrophilic polymer and a hydroxy propyl methylcellulose film coating material for protection.

The drug delivery system of the invention may be in any suitable dosage unit form.

A typical process for making the cefixime composition in accordance with this invention involves In step 1: the sifting using typically a vibrating sifter cefixime trihydrate powder, lactose, starch powders to obtain individual homogenous non lump containing free flowing particulate matter.

In step 2: granulation: Transferring. Cefixime Trihydrate, Lactose &. Starch (Maize) to a Planetary Mixer and mixing it for 10 minutes at slow speed. Adding slowly polyvinyl pyrrolidone (K-30) solution to contents of Planetary mixer at slow speed mixing, mixing the contents till uniform granular dough mass is formed. If necessary, additional wetting can be imparted with Isopropyl Alcohol. Transferring wet granules in Stainless Steel Trays of tray drier and drying at around 45° C. for about 5 hours. Drying further till the loss on drying comes within limit. Typically the granules are raked occasionally during drying. Sift the dried granules through 16 # sieve using Vibrosifter & the retained granules are passed through 1.5 mm screen using Multi mill at slow speed.

Step 3 lubrication of dry granules: The dry granules are transferred to a double cone blender. Sifted Methocel K-15M [HPMC], talcum and magnesium stearate are added to the cone blender and the mass in the blender are mixed for about 5 minutes.

Step 4 Slugging: the lubricated granules are transferred to a compression cubicle having an internal environment of temperature between 15 to 30 degrees Celsius and relative humidity below 55 percent. The lubricated granules are slugged by compression in the cubicle to obtain slugs of hardness 4 to 5 kg/sq cm.

Step 5 Deslugging the slugs are passed through 2.0 mm screen using multi mill at medium speed the deslugged granules are sifted through 16 mesh. The retained granules are passed through 1.5 mm screen using multi mill of slow speed.

Step 6 slug lubrication: the deslugged granules are transferred to a double cone blender. Cefixime Trihydrate powder, Sodium Lauryl Sulfate, Colloidal Silicon Dioxide (Aerosil—200), Talcum and Magnesium Stearate are sifted using a vibrating sifter. Cefixime Trihydrate powder, Sodium Lauryl Sulfate, Colloidal Silicon Dioxide (Aerosil—200), Talcum are added to the double cone blender. And the blender is operated for 10 minutes. The magnesium stearate is then added and blending is further continued for three minutes.

Step 7 core tablet compression: the lubricated deslugged granules are transferred to a compression cubicle having an internal environment of temperature between 15 to 30 degrees Celsius and relative humidity below 55 percent. The lubricated granules are tabletted by compression in the cubicle to obtain tablets of hardness not less than 3 kg/sq cms, average weight of around 640 mg, thickness of 4.4 to 4.8 mm and friability of not more than 1%.

Step 8 film coating of tablet cores: A coating pan is selected having an environment of: temperature between 20 to 30 degrees Celsius and relative humidity below 55% A homogenous solution of Methylene Chloride, Isopropyl Alcohol and HPMC and a plasticizer and titanium dioxide which collectively act as a coloring agent transferred to a sprayer placed near the pan the tablet cores are transferred into the coating pan and the tablet pan is heated by inching process using hot air blower. The initial temperature should not exceed 40° C. Once the tablet bed attains 40° C., it is ready for spray coating. The exhaust is started, and the tablets in the pan are sprayed with coating solution taking the following precautions.

1. Compressor pressure should not fall below 3 Kg/cm$^2$
2. Spraying should be stopped immediately, if the air pressure falls below 3 Kgs./Cm$^2$
3. Temperature of the tablet bed should be maintained at 40° C.
4. Continuous spraying from start to end would be preferred.
5. Avoid even slight over wetting.
6. Avoid dropping of coating solution directly into the coating pan.
7. Avoid spraying of the solution into blower, exhaust or to the uncovered part of the Coating pan since this will generate coating particles, which may stick to the tablet resulting in rough surfaces.
8. Powerful exhaust should be provided since it is dangerous to inhale the vapor of Methylene Chloride and IPA over a long period of time.

After the last coat of HPMC coloring agent solution is applied, drying of the tablet is continued for 15-20 minutes. Thereafter talcum is applied to the tablet bed to get the required gloss. The film-coated tablets are rolled for 5 minutes and then transferred to trays. In the trays the tablets are fried in tray drier at 50° C. for one to two hours to obtain dry film coated tablets in accordance with this invention.

In accordance with a preferred embodiment of the invention the hydrophilic polymer matrix comprises hydroxy propyl methyl cellulose together with flavonoids typically quercetin, genistein, naringin, diosmin, acacetin and chrysin which are added QS at step 2 during granulation. The flavonoids enhance the absorption of the drug in the G I tract.

In accordance with another aspect of the invention the drug delivery system includes the additive selected from salts, polyvinyl pyrrolidone, colloidal silicon dioxide, sodium lauryl sulfate, magnesium stearate, lactose & starch.

A drug delivery system according to this invention is in dosage unit form, typically, in the form of film coated extended release tablet, which may be coated with a pharmaceutically acceptable coating which in accordance with a preferred embodiment of the invention is of hydroxy propyl methyl cellulose with pharmaceutically acceptable solvents.

An important object of this invention is to improve patient compliance by minimizing the frequency of drug administration to once a day.

Another object of this invention is to provide a drug delivery system that will supply an immediate dose of cefixime trihydrate followed by sustained subsequent doses and which is 100% safe in the gastric system and is stable and not influenced by pH at any point.

A feature of the invention is that the drug delivery system is in the form of micro pulverized material, which is used to facilitate absorption, and at the same time the Matrix is inert. Yet another feature of the invention is that the delivery system is in a film coated tablet form, which facilitates:

Easy swallowing
Provides taste masking
Supreme stability
Excellent aesthetic looks The principal feature of the process of this invention involves imbedding granules/particles or other bioactive cefixime material in an inert hydrophilic polymeric or cellulosic matrix system such as in hydroxy propyl methylcellulose. A water sensitive molecule is used to make the tablet totally non aqueous.

The process of this invention involves granulation of the USP grade cefixime particulate material; along with excipients, starch and lactose to obtain granules of 16 to 20 mesh size. The granules are added to the polymer matrix base and slugged to imbed the active material in the matrix and deslugged through a sieve to achieve fragmented granules of 16 to 20-mesh size containing cefixime imbedded in the polymer matrix. These granules are compressed conventionally in a tablet compression machine at pressures ranging from 4 to 6 kg/sq cm to obtain the tablets of this invention which are film coated with a polymer such as HPMC to obtain a film coated tablet. Film coating further improves its Stability and Palatability.

The polymer matrix helps to regulate the release of cefixime in the systemic circulation such that the Minimum Effective Concentration is maintained for 24 hours. The initial 200 mg dose is made available in the first hour in the normal course.

EXAMPLE 1

30.36 Kgs of cefixime trihydrate powder, lactose 4.27 kgs, and 2.99 Kgs of starch were sifted separately using a vibrating sifter to obtain individual homogenous non lump containing free flowing powders. The powders were transferred to a Planetary Mixer and were mixed for 10 minutes at slow speed. 18 Kgs of Iso propyl alcohol together with 0.60 kgs of Polyvinyl pyrrolidone (K-30) were added slowly to the contents of Planetary mixer at slow speed mixing, and the contents were mixed till uniform granular dough mass was formed. The wet granules were transferred to Stainless Steel Trays of a tray drier and were dried at 45° C. for 5 hours. The granules were raked occasionally during drying. The dried granules were sifted through 16 # sieve using Vibrosifter & the retained granules were passed through 1.5 mm screen using Multi mill at slow speed. The dry granules were transferred to a double cone blender. 6.78 Kgs of sifted Methocel K-15M [HPMC], 0.35 of talcum powder and 0.35 Kgs of magnesium stearate were added to the cone blender and the mass in the blender was mixed for 5 minutes. The lubricated granules were transferred to a compression cubicle having an internal environment of temperature 20 degrees Celsius and relative humidity 50 percent. The lubricated granules were slugged by compression in the cubicle to obtain slugs of hardness 4.5 kg/sq cm. The slugs were passed through 2.0 mm screen using multi mill at medium speed and the deslugged granules were sifted through 16 mesh. The retained granules were passed through 1.5 mm screen using multi mill of slow speed. The deslugged granules were again transferred to a double cone blender. 17.1 Kgs of Cefixime Trihydrate powder, 0.60 kgs of Sodium Lauryl Sulfate, 0.30 Kgs of Colloidal Silicon Dioxide (Aerosil—200) as a glidant, and 0.35 kgs of Talcum powder and were sifted using a vibrating sifter and were added to the double cone blender and the blender was operated for 10 minutes. 0.35 kgs Magnesium Stearate was then added and blending were further continued for three minutes. The lubricated deslugged granules were transferred to a compression cubicle having an internal environment of temperature 25 degrees Celsius and relative humidity of 50 percent. The lubricated granules were tabletted by compression in the cubicle to obtain tablets of hardness 3.5 kg/sq cms, and an average weight of around 640 mg, thickness of 4.6 mm and friability of not more than 0.9%. 1,00,000 core tablets were transferred to a coating pan having an environment of: temperature 25 degrees Celsius and relative humidity below 45% A homogenous solution of 23 kgs Methylene Chloride, 9.0 kgs Isopropyl Alcohol and 1.5 kgs of HPMC and a plasticizer and titanium dioxide [insta-white IC-S-010] was transferred to a sprayer placed near the pan. The pan was heated by inching process using hot air blower. The initial temperature was maintained at 35 degrees Celsius. Once the tablet bed attained 40° C., the exhaust was started, and the tablets in the pan are sprayed with the coating solution to obtain coated tablets. Drying of the tablets was continued for 20 minutes and 50 Gms of talcum powder was added to provide gloss to the tablet. The tablet were rolled for 5 minutes and transferred to the trays of a drier and dried for one hour at 50 degrees Celsius, to obtain tablets in accordance with this invention.

EXAMPLE 2

30.38 Kgs of cefixime trihydrate powder, lactose 4.25 kgs, and 2.98 Kgs of starch 0.25 gms quercetin were sifted separately using a vibrating sifter to obtain individual homogenous non lump containing free flowing powders. The powders were transferred to a Planetary Mixer and were mixed for 10 minutes at slow speed. 18 Kgs of Iso propyl alcohol together with 0.60 kgs of Polyvinyl pyrrolidone (K-30) were added slowly to the contents of Planetary mixer at slow speed mixing, and the contents were mixed till uniform granular dough mass was formed. The wet granules were transferred to Stainless Steel Trays of a tray drier and were dried at 45° C. for 5 hours. The granules were raked occasionally during drying. The dried granules were sifted through 16 # sieve using Vibrosifter & the retained granules were passed through 1.5 mm screen using Multi mill at slow speed. The dry granules were transferred to a double cone blender. 4.78 Kgs of sifted Methocel K-15M [HPMC] 2.0 kgs of methylcellulose, 0.35 of talcum powder and 0.30 Kgs of stearic acid were added to the cone blender and the mass in the blender was mixed for 5 minutes. The lubricated granules were transferred to a compression cubicle having an internal environment of temperature 20 degrees Celsius and relative humidity 50 percent. The lubricated granules were slugged by compression in the cubicle to obtain slugs of hardness 4.5-kg/sq cm. The slugs were passed through 2.0 mm screen using multi mill at medium speed and the deslugged granules were sifted through 16 mesh. The retained granules were passed through 1.5 mm screen using multi mill of slow speed. The deslugged granules were again transferred to a double cone blender. 17.1 Kgs of Cefixime Trihydrate powder, 0.60 kgs of Sodium Lauryl Sulfate, 0.30 Kgs of Colloidal Silicon Dioxide (Aerosil—200), and 0.35 kgs of Talcum powder and were sifted using a vibrating sifter and were added to the double cone blender and the blender was operated for 10 minutes. 0.35 kg stearic acid was then added and blending was further continued for three minutes. The lubricated deslugged granules were transferred to a compression cubicle having an internal environment of temperature 25 degrees Celsius and relative humidity of 50 percent. The lubricated granules are tabletted by compression in the cubicle to obtain tablets of hardness 3.8 kg/sq cms, and an average weight of around 642 mg, thickness of 4.6 mm and friability of not more than 0.9%. 1,00,000 core tablets were transferred to a coating pan having an environment of: temperature 25 degrees Celsius and relative humidity below 45% A homogenous solution of 23 kgs Methylene Chloride, 9.0 kgs Isopropyl Alcohol and 1.5 kgs of methyl cellulose and a plasticizer and titanium dioxide [insta-white IC-S-010] was transferred to a sprayer placed near the pan. The pan was heated by inching process using hot air blower. The initial temperature was maintained at 35 degrees Celsius. Once the tablet bed attained 40° C., the exhaust was started, and the tablets in the pan are sprayed with the coating solution to obtain coated tablets. Drying of the tablets was continued for 20 minutes and 50 Gms of talcum powder was added to provide gloss to the tablet. The tablet were rolled for 5 minutes and transferred to the trays of a drier and dried for one hour at 50 degrees Celsius, to obtain tablets in accordance with this invention.

EXAMPLE 3

30.36 Kgs of cefixime trihydrate powder, lactose 4.27 kgs, and 2.99 Kgs of starch 50 gms of genistein were sifted separately using a vibrating sifter to obtain individual homogenous non lump containing free flowing powders. The powders were transferred to a Planetary Mixer and were mixed for 10 minutes at slow speed. 18 Kgs of Iso propyl alcohol together with 0.70 kg of Polyvinyl pyrrolidone (K-30) were added slowly to the contents of Planetary mixer at slow speed mixing, and the contents were mixed till uniform granular dough mass was formed. The wet granules were transferred to Stainless Steel Trays of a tray drier and were dried at 45° C. for 5 hours. The granules were raked occasionally during drying. The dried granules were sifted through 16 # sieve using Vibrosifter & the retained granules were passed through 1.5 mm screen using Multi mill at slow speed. The dry granules were transferred to a double cone blender. 6.25 Kgs HPMC and 0.5 kgs of ethyl cellulose sifted, 0.35 of talcum powder and 0.35 Kgs of magnesium stearate were added to the cone blender and the mass in the blender was mixed for 5 minutes. The lubricated granules were transferred to a compression cubicle having an internal environment of temperature 20 degrees Celsius and relative humidity 50 percent. The lubricated granules were slugged by compression in the cubicle to obtain slugs of hardness 5-kg/sq cm. The slugs were passed through 2.0 mm screen using multi mill at medium speed and the deslugged granules were sifted through 16 mesh. The retained granules were passed through 1.5 mm screen using multi mill of slow speed. The deslugged granules were again transferred to a double cone blender. 17.2 Kgs of Cefixime Trihydrate powder, 0.70 kgs of Sodium Lauryl Sulfate, 0.35 Kgs of Colloidal Silicon Dioxide (Aerosil—200), and 0.35 kg of Talcum powder and were sifted using a vibrating sifter and were added to the double cone blender and the blender was operated for 10 minutes. 0.40 kgs Magnesium Stearate was then added and blending was further continued for three minutes. The lubricated deslugged granules were transferred to a compression cubicle having an internal environment of temperature 25 degrees Celsius and relative humidity of 50 percent. The lubricated granules are tableted by compression in the cubicle to obtain tablets of hardness 3.5 kg/sq cms, and an average weight of around 645 mg, thickness of 4.6 mm and friability of not more than 0.7%. 1,00,000 core tablets were transferred to a coating pan having an environment of: temperature 25 degrees Celsius and relative humidity below 45% A homogenous solution of 23.5 kgs Methylene Chloride, 9.0 kgs Isopropyl Alcohol and 1.5 kgs of HPMC and ethyl cellulose and a plasticizer and titanium dioxide [insta-white IC-S-010] was transferred to a sprayer placed near the pan. The pan was heated by inching process using hot air blower. The initial temperature was maintained at 35 degrees Celsius. Once the tablet bed attained 40° C., the exhaust was started, and the tablets in the pan are sprayed with the coating solution to obtain coated tablets. Drying of the tablets was continued for 20 minutes and 50 Gms of talcum powder was added to provide gloss to the tablet. The tablet were rolled for 5 minutes and transferred to the trays of a drier and dried for one hour at 50 degrees Celsius, to obtain tablets in accordance with this invention.

Bioavailability Studies

A randomized two way two period two treatment cross over bioavailability study of the tablets produced as above was carried on healthy male adult human volunteers under fasting condition. Comparison was done with conventional 200 mg cefixime tablet administered twice daily.

Figure 2:
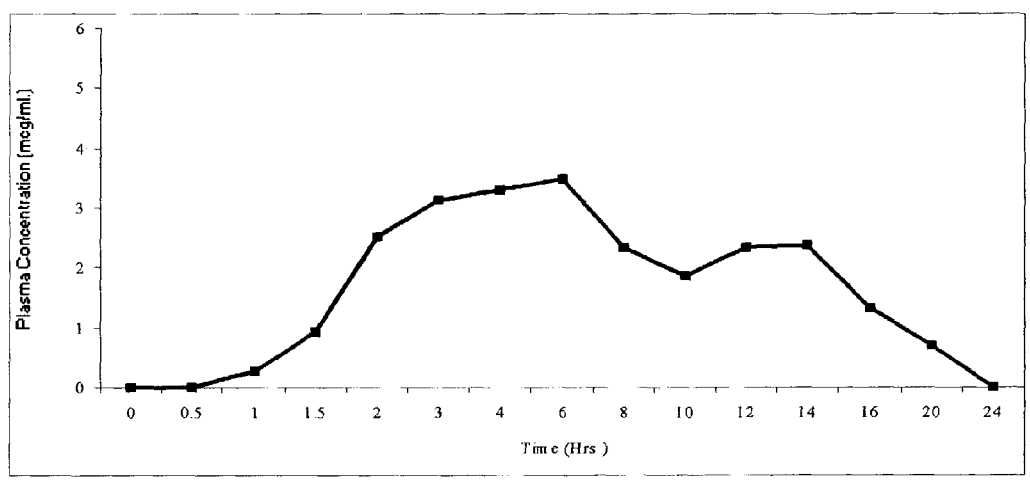
FIG. 2 illustrates plasma concentrations resulting from administration of cefixime described in Example 1.
Figure 3:
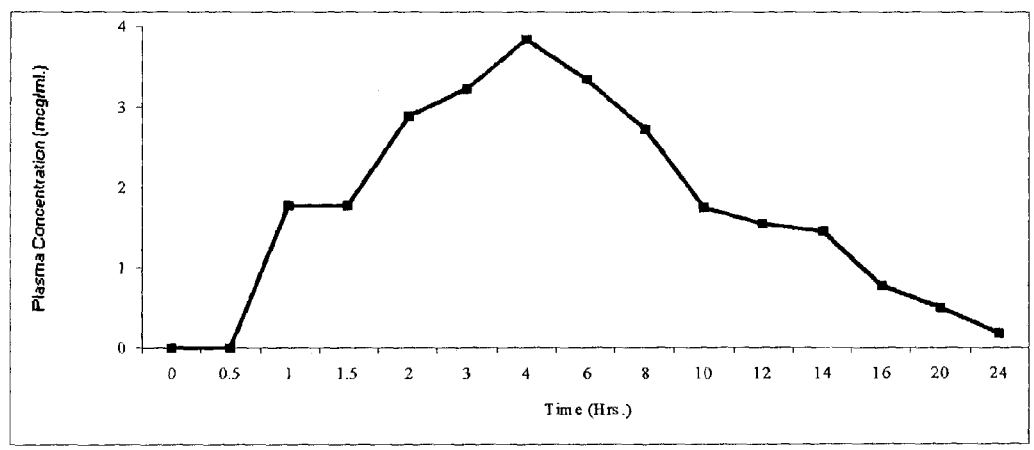
FIG. 3 illustrates plasma concentrations resulting from administration of cefixime described in Example 2.
Figure 4:
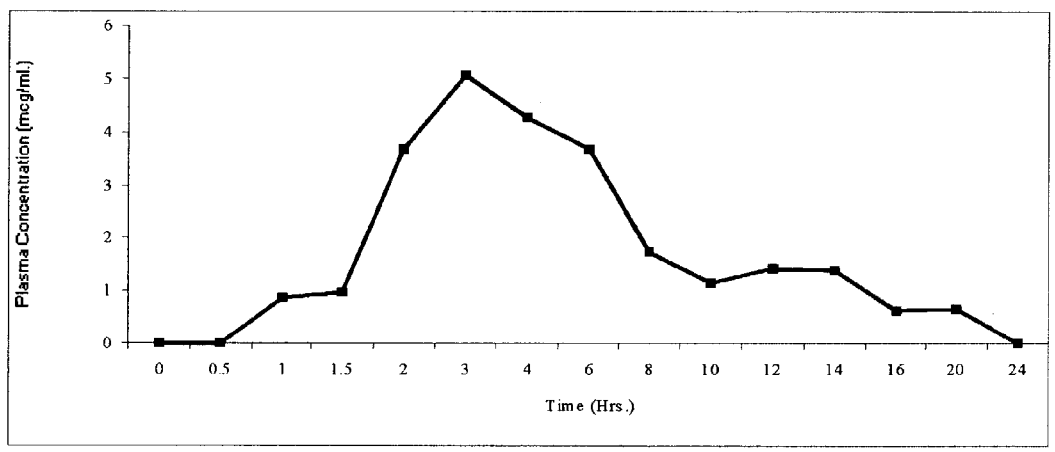
FIG. 4 illustrates plasma concentrations resulting from administration of cefixime described in Example 3.

Typical plasma concentration of the drug in a dispersible tablet delivery system on a twice-daily administered dose is seen in FIG. 1 of the accompanying drawing. The two peaks representing the increase in plasma concentration in mg/ml after each administration. FIGS. 2, 3 and 4 represent the bioavailability of the drug representative of the three examples: example 1, 2 and 3 respectively above. As can be seen from the graphs the plasma concentration is uniformly higher in all three cases with reference to the conventional as seen in FIG. 1. Addition of flavonoids increases the bioavailability marginally as seen in FIGS. 3 and 4 of the accompanying drawings.

While emphasis has been placed herein on the structure of the tablet in the process of manufacture thereof it will be appreciated that many embodiments can be made and that many changes can be made in the preferred embodiments without departing from the principals of the invention. These and other changes in the preferred embodiment as well as other embodiments of the invention will be apparent to those skilled in the art from the disclosure herein, whereby it is to be distinctly understood that the foregoing descriptive matter is to be interpreted merely as illustrative of the invention and not as a limitation.

The invention claimed is:

1. An extended-release oral film-coated tablet comprising cefixime trihydrate, a hydrophilic matrix, starch, lactose and a surfactant, wherein about two-thirds of the mass of cefixime trihydrate is embedded in the hydrophilic matrix and the remaining about one-third is in free form, and wherein said film-coated tablet is suitable for once-a-day dosing.

2. The film-coated tablet of claim 1, wherein the hydrophilic matrix comprises one or more hydrophilic cellulose derivatives.

3. The film-coated tablet of claim 1, wherein the hydrophilic matrix comprises a hydrophilic polymer selected from the group consisting of: methyl cellulose, hydroxypropyl methylcellulose, hydroxyethyl cellulose, hydroxypropyl cellulose, carboxymethyl cellulose, sodium carboxymethyl cellulose and hydroxyethyl methyl cellulose, polyacrylamide derivatives, proteins, alginates, arabinogalactane, chitosan and methacrylic acid derivatives, alone or in any combination.

4. The film-coated tablet of claim 1, wherein the hydrophilic matrix comprises hydroxy propyl methyl cellulose.

5. The film-coated tablet of claim 1, further comprising a flavonoid selected from the group consisting of: quercetin, genistein, naringin, diosmin, acacetin and chrysin, alone or in any combination.

6. The film-coated tablet of claim 1, further comprising a pharmaceutical excipient selected from the group consisting of: polyvinyl pyrrolidone, colloidal silicon dioxide, and magnesium stearate, alone or in any combination.

7. The film-coated tablet of claim 1, wherein said coating comprises hydroxy propyl methyl cellulose.

8. The film-coated tablet of claim 1, wherein said tablet comprises 400 mg of cefixime trihydrate.

9. The film-coated tablet of claim 1, wherein the surfactant comprises sodium lauryl sulfate.

* * * * *